United States Patent [19]

Manning et al.

[11] Patent Number: 5,693,465

[45] Date of Patent: Dec. 2, 1997

[54] METHODS FOR PREDICTING THE BEHAVIOUR OF BREAST TUMOURS

[75] Inventors: David Lockwood Manning; Robert Ian Nicholson; Julia Margaret Wendy Gee, all of Cardiff; Christopher Douglas Green, Birkenhead, all of Great Britain

[73] Assignee: University of Wales College of Medicine, Cardiff, United Kingdom

[21] Appl. No.: 311,023

[22] Filed: Sep. 22, 1994

[51] Int. Cl.$^6$ .............................. C12Q 1/68; C12P 19/34; C07K 15/28; C07K 13/00

[52] U.S. Cl. .............................. 435/6; 435/91.2; 435/7.1; 435/7.2; 435/7.9; 435/69.1; 536/23.1; 536/24.3; 536/24.33; 530/388.1; 530/300; 530/350

[58] Field of Search .................... 435/6, 7.1, 7.2, 435/7.9, 91.2, 69.1; 536/23.1, 24.3–24.33, 24.5; 514/44; 530/388.1

[56] References Cited

PUBLICATIONS

Gura, Science 270:575–577, 1995.
James, Antiviral Chemistry and Chemotherapy 2:191–214.
Guiterrez, The Lancet 339:715–721, 1992.
Talmadge, Adv. Drug Delivery Reviews 10:247–299, 1993.
Sigma Catalog, 1992.
Freeman et al., Advanced Drug Delivery Reviews 12: 169–183, 1993.

*Primary Examiner*—W. Gary Jones
*Assistant Examiner*—Dianne Rees
*Attorney, Agent, or Firm*—Young & Thompson

[57] ABSTRACT

The estrogen-regulated gene sequence pLIV1 has been discovered and isolated, and found to be significantly associated with the metastatic spread of breast cancer cells to the regional lymph nodes. Methods are therefore provided for determining the risk of metastasis of a female breast tumour, as well as for predicting the responsiveness to endocrine treatment of a female breast tumour, which involve determining whether a tissue sample from a tumour expresses a polypeptide containing the pLIV1 gene sequence, or a substantial portion thereof.

20 Claims, 2 Drawing Sheets

```
5'
     G   F   I   A       T   S   I         I   S   F         L   S   L   L         G   V   I         L   V   P           20
     GGTTTTATAG          CCATTTCCAT         CATCAGTTTC        CTGTCTCTGC            TGGGGGTTAT       CTTAGTGCCT            60
     L   M   N   R       V   F   F         K   F   L         L   S   F   L         V   A   L         A   V   G           40
     CTCATGAATC          GGGTGTTTTT         CAAATTTCTC        CTGAGTTTCC            TTGTGGCACT       GGCCGTTGGG           120
     T   L   S   G       D   A   F         L   H   L         L   P   H   S         H   A   S         H   H   H           60
     ACTTTGAGTG          GTGATGCTTT         TTTACACCTT        CTTCCACATT            CTCATGCAAG       TCACCACCAT           180
     S   H   S   H       E   E   P         A   M   E         M   K   R   G         P   L   F         S   H   L           80
     AGTCATAGCC          ATGAAGAACC         AGCAATGGAA        ATGAAAAGAG            GACCACTTTT       CAGTCATCTG           240
     S   S   Q   N       I   E   E         S   A   Y         F   D   S   T         W   K   G         L   T   A          100
     TCTTCTCAAA          ACATAGAAGA         AAGTGCCTAT        TTTGATTCCA            CGTGGAAGGG       TCTAACAGCT           300
     L   G   G   L       Y   F   M         F   L   V         E   H   V   L         T   L   I         K   Q   F          120
     CTAGGAGGCC          TGTATTTCAT         GTTTCTTGTT        GAACATGTCC            TCACATTGAT       CAAACAATTT           360
                                                                1003
     K   D   K   K      |K   K   N         Q   K   K         P   E   N   D         D   D   V         E|  I   K          140
     AAAGATAAGA          AGAAAAGAA          TCAGAAGAAA        CCTGAAAATG            ATGATGATGT       GGAGATTAAG           420
     K   Q   L   S       K   Y   E         S   Q   L         S   T   N   E         E   K   V         D   T   D          160
     AAGCAGTTGT          CCAAGTATGA         ATCTCAACTT        TCAACAAATG            AGGAGAAAGT       AGATACAGAT           480
     D   R   T   E       G   Y   L         R   A   D         S   Q   E   P         S   H   F         D   S   Q          180
     GATCGAACTG          AAGGCTATTT         ACGAGCAGAC        TCACAAGAGC            CCTCCCACTT       TGATTCTCAG           540
     Q   P   A   V       L   E   E         E   E   V         M   I   A   H         A   H   P         Q   E   V          200
     CAGCCTGCAG          TCTTGGAAGA         AGAAGAGGTC        ATGATAGCTC            ATGCTCATCC       ACAGGAAGTC           600
     Y   N   E   Y       V   P   R         G   C   K         N   K   C   H         S   H   F         H   D   T          220
     TACAATGAAT          ATGTACCCAG         AGGGTGCAAG        AATAAATGCC            ATTCACATTT       CCACGATACA           660
     L   G   Q   S       D   D   L         I   H   H         H   H   D   Y         H   H   I         L   H   H          240
     CTCGGCCAGT          CAGACGATCT         CATTCACCAC        CATCATGACT            ACCATCATAT       TCTCCATCAT           720
                                                                                       1004
     H   H   H   Q       N   H   H         P   H   S         H  |S   Q   R         Y   S   R         E   E   L          260
     CACCACCACC          AAAACCACCA         TCCTCACAGT        CACAGCCAGC            GCTACTCTCG       GGAGGAGCTG           780
    |K   D   A   G       V|  A   T         L   A   W         M   V   M             G   D   G         L   H   N          280
     AAAGATGCCG          GCTCGCCAC          TTTGGCCTGG        ATGGTGATAA            TGGGTGATGG       CCTGCACAAT           840
     F   S   D   G       L   A   I         G   A   A         F   T   E   G         L   S   S         G   L   S          300
     TTCAGCGATG          GCCTAGCAAT         TGGTGCTGCT        TTTACTGAAG            GCTTATCAAG       TGGTTTAAGT           900
     T   S   V   A       V   F   C         H   E   L         P   H   E   L         G   D   F         A   V   L          320
     ACTTCTGTTG          CTGTGTTCTG         TCATGAGTTG        CCTCATGAAT            TAGGTGACTT       TGCTGTTCTA           960
     L   K   A   G       M   T   V         K   Q   A         V   L   Y   N         A   L   S         A   M   L          340
     CTAAAGGCTG          GCATGACCGT         TAAGCAGGCT        GTCCTTTATA            ATGCATTGTC       AGCCATGCTG          1020
     A   Y   L   G       M   A   T         G   I   F         I   G   H   Y         A   E   N         V   S   M          360
     GCGTATCTTG          GAATGGCAAC         AGGAATTTTC        ATTGGTCATT            ATGCTGAAAA       TGTTTCTATG          1080
     W   I   F   A       L   T   A         G   L   F         M   Y   V   A         L   V   D         M   V   P          380
     TGGATATTTG          CACTTACTGC         TGGCTTATTC        ATGTATGTTG            CTCTGGTTGA       TATGGTACCT          1140
     E   M   L   H       N   D   A         S   D   H         G   C   S   R         W   G   Y         F   F   L          400
     GAAATGCTGC          ACAATGATGC         TAGTGACCAT        GGATGTAGCC            GCTGGGGGTA       TTTCTTTTTA          1200
     Q   N   A   G       M   L   L         G   F   G         I   M   L   L         I   P   Y        |L   N   I          420
     CAGAATGCTG          GGATGCTTTT         GGGTTTTGGA        ATTATGTTAC            TTATTCCATA       TTTGAACATA          1260
               1005
    |K   S   C   S       Y   K   F         L   V   K         V| STOP 320
     AAATCGTGTT          CGTATAAATT         TCTAGTTAAG        GTTTAAATGC            TAGAGTAGCT............3'            1320
```

FIG. 1

(SEQ ID NO: 1)

```
5'
GGTTTTATAG CCATTTCCAT CATCAGTTTC CTGTCTCTGC TGGGGGTTAT CTTAGTGCCT    60
CTCATGAATC GGGTGTTTTT CAAATTTCTC CTGAGTTTCC TTGTGGCACT GGCCGTTGGG   120
ACTTTGAGTG GTGATGCTTT TTTACACCTT CTTCCACATT CTCATGCAAG TCACCACCAT   180
AGTCATAGCC ATGAAGAACC AGCAATGGAA ATGAAAAGAG GACCACTTTT CAGTCATCTG   240
TCTTCTCAAA ACATAGAAGA AAGTGCCTAT TTTGATTCCA CGTGGAAGGG TCTAACAGCT   300
CTAGGAGGCC TGTATTTCAT GTTCTTGTT GAACATGTCC TCACATTGAT CAAACAATTT    360
AAAGATAAGA AGAAAAAGAA TCAGAAGAAA CCTGAAAATG ATGATGATGT GGAGATTAAG   420
AAGCAGTTGT CCAAGTATGA ATCTCAACTT TCAACAAATG AGGAGAAAGT AGATACAGAT   480
GATCGAACTG AAGGCTATTT ACGAGCAGAC TCACAAGAGC CCTCCCACTT TGATTCTCAG   540
CAGCCTGCAG TCTTGGAAGA AGAAGAGGTC ATGATAGCTC ATGCTCATCC ACAGGAAGTC   600
TACAATGAAT ATGTACCCAG AGGGTGCAAG AATAAATGCC ATTCACATTT CCACGATACA   660
CTCGGCCAGT CAGACGATCT CATTCACCAC CATCATGACT ACCATCATAT TCTCCATCAT   720
CACCACCACC AAAACCACCA TCCTCACAGT CACAGCCAGC GCTACTCTCG GAGGAGCTG    780
AAAGATGCCG GCGTCGCCAC TTTGGCCTGG ATGGTGATAA TGGGTGATGG CCTGCACAAT   840
TTCAGCGATG GCCTAGCAAT TGGTGCTGCT TTTACTGAAG GCTTATCAAG TGGTTTAAGT   900
ACTTCTGTTG CTGTGTTCTG TCATGAGTTG CCTCATGAAT TAGGTGACTT TGCTGTTCTA   960
CTAAAGGCTG GCATGACCGT TAAGCAGGCT GTCCTTTATA ATGCATTGTC AGCCATGCTG  1020
GCGTATCTTG GAATGGCAAC AGGAATTTTC ATTGGTCATT ATGCTGAAAA TGTTTCTATG  1080
TGGATATTTG CACTTACTGC TGGCTTATTC ATGTATGTTG CTCTGGTTGA TATGGTACCT  1140
GAAATGCTGC ACAATGATGC TAGTGACCAT GGATGTAGCC GCTGGGGGTA TTTCTTTTTA  1200
CAGAATGCTG GGATGCTTTT GGGTTTTGGA ATTATGTTAC TTATTCCATA TTTGAACATA  1260
AAATCGTGTT CGTATAAATT TCTAGTTAAG GTTAAATGC TAGAGTAGCT TAAAAAGTTG   1320
TCATAGTTTC AGTAGGTCAT AGGGAGATGA GTTTGTATGC TGTACTATGC AGCGTTTAAA  1380
GTTAGTGGGT TTTGTGATTT TTGTATTGAA TATTGCTGTC TGTTACAAAG TCAGTTAAAG  1440
GTACGTTTTA ATATTTAAGT TATTCTATCT TGGAGATAAA ATCTGTATGT GCAATTCACC  1500
GGTATTACCA GTTTATTATG TAAACAAGAG ATTTGGCATG ACATGTTCTG TATGTTTCAG  1560
GGAAAAATGT CTTTAATGCT TTTTCAAGAA CTAACACAGT TATTCCTATA CTGGATTTTA  1620
GGTCTCTGAA GAACTGCTGG TGTTTAGGAA TAAGAATGTG CATGAAGCCT AAAATACCAA  1680
GAAAGCTTAT ACTGAATTTA AGCAAAGAAA TAAAGGAGAA AAGAGAAGAA TCTGAGAATT  1740
GGGGAGGCAT AGATTCTTAT AAAAATCACA AAATTTGTTG TAAATTAGAG GGGAGAAATT  1800
TAGAATTAAG AAAAAAAAGG CAGAATTAGT ATAGAGTACA TTCATTAAAC ATTTTTGTCA  1860
GGATTATTTC CCGTAAAAAC GTAGTGAGCA CTCTCATATA CTAATTAGTG TACATTTAAC  1920
TTTGTATAAT ACAGAAATCT AAATATATTT AATGAATTCA AGCAATATAC ACTTGACCAA  1980
GAAATTG&AA TTTCAAAATG TTCGTGCGGG TTATATACCA GATGAGTACA GTGAGTAGTT  2040
TATGTATCAC CAGACTGGGT TATTGCCAAG TTATATATCA CCAAAAGCTG TATGACTGGA  2100
TGTTCTGGTT ACCTGGTTTA CAAAATTATC AGAGTAGTAA AACTTTGATA TATATGAGGA  2160
TATTAAAACT ACACTAAGTA TCATTTGATT CGATTCAGAA AACTTTGATA TATATGAGGA  2220
TATTAAAACT ACACTAAGTA TCATTTGATT CGATTCAGAA AGTACTTTGA TATCTCTCAG  2280
TGCTTCAGTG CTATCATTGT GAGCAATTGT CTTTATATAC GGTACTGTAG CCATACTAGG  2340
CCTGTCTGTG GCATTCTCTA GATGTTTCTT TTTTACACAA TAAATTCCTT ATATCAGCTT  2400
GAAA                                                              2404   3'
```

FIG. 2

(SEQ ID NO: 3)

METHODS FOR PREDICTING THE BEHAVIOUR OF BREAST TUMOURS

This invention relates to methods for predicting the behaviour of breast tumours and in particular, but not exclusively, to methods in which a breast tumour sample is examined for expression a specified gene sequence thereby to indicate responsiveness to anti-hormonal therapies and/or to indicate the propensity for metastatic spread.

BACKGROUND OF THE INVENTION

Breast cancer is the most common malignant disease in women in the UK, with 27,000 new cases per year and about 1,000,000 per year worldwide. At clinical presentation, approximately 50% of the tumours are sensitive to female hormones and may be treated by therapies which interfere with their cellular actions. A number of different biochemical and tumour markers are currently used to determine the hormonal sensitivity of the breast tumours and thereby dictate the type of therapy offered. One of these, the oestrogen receptor (ER) is particularly useful in predicting the responsiveness of locally advanced and oetastatic disease to antihormonal therapies, with patients with receptor positive disease (ER+) more frequently responding to treatment than when their tumours are receptor negative (ER-).

Approximately 70% of breast cancers are ER+, unfortunately however, the association between ER expression and endocrine sensitivity is not absolute with only about half of those ER+ patients showing any response. It is thought that this failure is due to the presence of detectable but mutated receptors. Consequently, the search for additional markers of oestrogen responsiveness has been pursued. The detection of cellular products of oestrogen regulated genes in ER+ disease would suggest a functional ER system and hence a sensitivity to endocrine treatments.

In this light, we have isolated a series of oestrogen-regulated genes of which two of the gene sequences—pLIV1 and pLIV2 (pS2)—are significantly associated with ER+ disease and as such are believed to indicate ER functionality and hence responsiveness to endocrine therapy. The partial nucleotide sequence and predicted amino acid sequence of pLIV1 is set out in FIG. 1 of the accompanying drawings with FIG. 2 including further nucleotide sequence data. Interestingly however and despite their oestrogen inducibility, we found that pLIV1 and pS2 were not always co-expressed in ER+ breast cancers; an observation that suggested additional and gene specific regulatory elements which may relate to the different functional roles of these gone products. This concept has been supported by the methods set out below where we have examined the expression of pLIV1 and pS2 in relation to various clinical and histopathological features of breast cancer and have shown that pLIV1 but not pS2, is significantly associated with the metastatic spread of breast cancer cells to the regional lymph-nodes.

SUMMARY OF THE INVENTION

In one aspect, this invention provides a method of predicting the propensity for metastatic spread of a breast tumour, which comprises examining a tissue sample from said tumour for expression of a polypeptide containing at least a substantial part of the amino acid sequence designated pLIV1 in FIG. 1 of the accompanying drawings or a polypeptide homologous therewith.

In another aspect, this invention provides a method of predicting the responsiveness to endocrine therapy of a breast tumour, which comprises examining a tissue sample from said tumour for expression of a polypeptide containing at least a substantial part of the amino acid sequence designated pLIV1 in FIG. 1 of the accompanying drawings, or a polypeptide homologous therewith.

Expression of the polypeptides may be determined directly or indirectly. For example, the sample may be contacted with an antibody (monoclonal or polyclonal) specific to the selected polypeptide. Alternatively, the sample may be contacted with a nucleic acid hybridization probe capable of hybridising with the mRNA corresponding the selected polypeptide. Still further, the sample may be subjected to a Northern blotting technique to examine for mRNA, indicating expression of the polypeptide. For those techniques in which the mRNA is detected, the sample may be subjected to a nucleic acid amplification process whereby the mRNA molecule or a selected part thereof is amplified using appropriate nucleotide primers.

The studies by the applicants identify pLIV1 as a candidate gene for the hormonal regulation of tumour invasion of breast cancer, as a prognostic marker of metestatic spread and as a suitable target for therapeutic intervention byantihormones and antibody directed measures.

It will be appreciated that these methods include the possibility of determining the effectiveness of anti-hormonal treatments by monitoring pLIV1 expression, and the development of anti-hormones and antibodies for therapeutics.

The invention also extends to antibodies specific to the polypeptide pLIV1 and to kits incorporating such antibodies.

LIST OF FIGURES

FIG. 1 is a listing of the nucleotide partial sequence (SEQ ID NO:1) and corresponding predicted amino acid sequence (SEQ ID NO:2) for the pLIV1 gene;

FIG. 2 is a listing of the nucleotide partial sequence of FIG. 1 but extending further in the 3' direction (SEQ ID NO:3).

DESCRIPTION OF PREFERRED EMBODIMENTS

Tumour samples were obtained from 74 patients presenting during 1990 with primary breast cancer at the City Hospital in Nottingham, United Kingdom, under the care of Professor R W Blamey. A simple or subcutaneous mastectomy was undertaken and lymph node biopsy samples removed from the lower axilla, from the apex of the axilla, and from the internal mammary chain. Patients with tumour cells histologically evident in any node were classified as lymph node positive. The menopausal status and age at mastectomy of each patient were recorded in addition to tumour size. Histological grade of malignancy was assessed in all tumours by using a modification of Bloom and Richardson's criteria as described in Elston C W and Ellis I O Pathological prognostic factors in breast cancer—The value of histological grade in breast cancer-Experience from a large study with follow up. Histopathology 19 403–410 (1991). Tumours were graded I to III with increasing loss of differentiation. The mitotic activity of tumours was assessed by counting the number of mitotic figures in 10 or 20 high power fields at the peripheral infiltrating margin of the tumour. Grades I–III corresponded to 0–9, 10–19 and over 20 mitotic figures/10 high power fields respectively.

TISSUE ANALYSIS

Immediately after surgery the tissue was snap-frozen and stored in liquid nitrogen before transportation in dry ice to the Tenovus Centre, Cardiff, United Kingdom. Samples were stored at −70° C. until assay.

The assay procedures for the measurement of ER by immunohistochemical analysis using the ER rat monoclonal antibody H222spg and pLIV1 and pS2 by Northern analysis are described in Walker K J, Bouzubar N, Robertson J F R, Ellis I O, Elston C W, Blamey R W, Wilson D W, Griffiths K, and Nicholson R I "Immunocytochemical localization of oestrogen receptors in human breast tissue". Cancer Research 1988 48 6517–6522; and Manning D L, McClelland R A, Gee J M, Chan C M W, Green C D, Blamey R W, and Nicholson R I "The role of four oestrogen responsive genes, pLIV1, pS2, pSYD3 and pSYD8, in predicting responsiveness to endocrine therapy in primary breast cancer". Eur J Cancer 1993 29A 1462–1468, the contents of which are incorporated herein by reference.

Briefly the specimen evaluation for ER was performed on an Olympus microscope (BH-2) using an ocular magnification of ×40. Control slides (control rat IgG antibody) were checked for non-specific binding. Tumours were classified as ER positive where >5% of tumour cells were stained for the receptor. Northern analysis of RNA from each tumour and densitometric assessment of the 4.4 kb pLIV1 and 0.6 kb pS2 mRNA transcript were performed and a cut-off value (to exclude background hybridization) were assigned as previously described in Lovekin C, Ellis I O, Locker A, Robertson J F R, Bell J, Nicholson R I, Gullick W J, Elston C W, and Blamey R W "c-erbB2 oncoprotein expression in primary and advanced breast cancer". Br.J. Cancer 1991 63 439–443.

STATISTICAL ANALYSIS

Chi squared contingency tables with Yates correction factor were used to compare subgroups of the tumour population.

PRODUCTION AND USE OF ANTIBODIES TO THE pLIV1 GENE PRODUCT

The original pLIV1 sequence was extended via a primer directed cloning strategy to generate a 2.3 kb clone. Computer-assisted analysis of the predicted amino acid sequence of its gene product identified three peptides (1003, amino acids 125–138 of SEQ ID NO: 2 1004 amino acids 252–265 of SEQ ID NO:2 and 1005 amino acid 418–431 of SEQ ID NO:2 on FIG. 1) each of 14 amino acids which we have used to raise polyclonal antibodies in New Zealand white rabbits using multiple antigenic peptides. The peptides 1004 and 1005 were found to be most immunogenic, generating ELISA positive sera at dilutions of 1/200,000. Cross-reactivity studies using the three peptides have identified 7 positive specific sera.

Analysis of these sera in a labelled avidin Immunocytochemical procedure designed to minimise background staining has shown the pLIV1 protein product to be expressed in the cytosol of ER+ epithelial cells of breast tumours. A good correlation has been obtained between the immunohistochemical localisation of the pLIV1 gene product and its mRNA, as determined by either in situ hybridisation or Northern analysis. Importantly, initial studies do not suggest that the pLIV1 gene is highly expressed in normal tissues or in non-invasive in situ carcinomas.

TABLE 1

|  | no. of patients | percentage |
|---|---|---|
| M. status |  |  |
| pre- | 31 | 42 |
| post- | 43 | 58 |
| ER status |  |  |
| ER+ | 47 | 63 |
| ER− | 27 | 27 |
| Nodal Status |  |  |
| N-negative | 45 | 61 |
| N-positive | 29 | 38 |
| GRADE |  |  |
| I | 16 | 22 |
| II | 25 | 34 |
| III | 33 | 44 |
| SIZE |  |  |
| <2 cm | 53 | 72 |
| >2 cm | 21 | 28 |
| Vasc. Inv. |  |  |
| negative | 51 | 69 |
| positive | 23 | 31 |

The data presented in Table 1 shows the clinical (lymph node status, menopausal status and tumour size) pathological (histological grade and vascular invasion) and biochemical (oestrogen receptor status) features of the primary tumours used in the current study.

TABLE 2

|  | pLIV1+ | pLIV1− | p value | pS2+ | pS2− | p value |
|---|---|---|---|---|---|---|
| M. status |  |  |  |  |  |  |
| pre- | 13 | 18 | n.s. | 14 | 17 | <0.01 |
| post- | 13 | 30 |  | 10 | 33 |  |
| STAGE |  |  |  |  |  |  |
| N-negative | 10 | 35 | <0.01 | 12 | 33 | n.s. |
| N-positive | 16 | 13 |  | 12 | 17 |  |
| GRADE |  |  |  |  |  |  |
| I | 4 | 12 |  | 4 | 12 |  |
| II | 12 | 13 | n.s. | 9 | 16 | n.s. |
| III | 10 | 23 |  | 11 | 22 |  |
| SIZE |  |  |  |  |  |  |
| <2 cm | 17 | 38 | n.s. | 20 | 34 | n.s. |
| >2 cm | 9 | 12 |  | 4 | 18 |  |
| Vasc. Inv. |  |  |  |  |  |  |
| negative | 15 | 38 | n.s. | 13 | 38 | n.s. |
| positive | 11 | 12 |  | 11 | 12 |  |

Examination of the relationship between the clinical and pathological data (Table 2) revealed significant associations between pLIV1 and lymph node involvement (p<0.01) and pS2 with menopausal status (p<0.01). Thus while 55% lymph node positive patients were pLIV1 positive, only 10/45 (22%) lymph node negative patients showed evidence for expression of this gene sequence. No other relationships were significant.

As we had previously found, the pLIV1 and pS2 genes were most frequently detected in ER+ disease (where pLIV1 was expressed in 51% of ER+ tumours compared to only 7% of ER− tumours and pS2 was similarly observed in 47% of MR+ tumours compared to 7% of ER− tumours).

Consequently, the expression of these genes was further examined in the ER+ subset of patients (Table 3).

TABLE 3

|  | ER+ pLIV1+ | ER− pLIV1− | p value | ER+pS2→ | ER+pS2− | p value |
|---|---|---|---|---|---|---|
| M. status. |  |  |  |  |  |  |
| pre- | 12 | 10 | n.s. | 13 | 9 | =0.06 |
| post- | 12 | 13 |  | 9 | 16 |  |
| STAGE |  |  |  |  |  |  |
| N-negative | 9 | 20 | <0.001 | 12 | 17 | n.s. |
| N-positive | 15 | 3 |  | 10 | 8 |  |
| Vasc. Inv. |  |  |  |  |  |  |
| negative | 14 | 19 | n.s. | 13 | 20 | n.s. |
| positive | 10 | 4 |  | 9 | 5 |  |

Significantly, the relationship between pLIV1 and lymph node involvement was strengthened (p<0.001) by the exclusion of the ER− tumours. A total of 15/24 (63%) ER+pLIV1+tumours showed nodal involvement while 20/23 (87%) ER+pLIV1-tumours were lymph node negative. The association of pS1 and menopausal status did not reach significance in ER+ disease while insufficient numbers (2/27) precluded further analysis of pLIV1 and pS2 expression in ER negative disease (data not included). In addition, no significant relationship was observed between pLIV1 or pS2 and vascular invasion.

Subdivision of the data shown in Table 3 by the pLIV1 independent variable of tumour size showed pLIV1 expression to be highly predictive of lymph node involvement in small cancers (<2.0 cm): 92% patients with lymph node involvement were pLIV1 positive while only 23% lymph node negative patients were pLIV1 positive (Table 4).

TABLE 4

|  | ER+pLIV1− | ER+pLIV1+ | p value |
|---|---|---|---|
| Tumour size (<2 cm) |  |  |  |
| N− | 17 | 5 | <0.001 |
| N+ | 1 | 11 |  |
| Tumour size (>2 cm) |  |  |  |
| N− | 3 | 3 | n.s. |
| N+ | 2 | 5 |  |
| GRADE I |  |  |  |
| N− | 8 | 2 | n.s. |
| N+ | 1 | 1 |  |
| GRADE II |  |  |  |
| N− | 6 | 4 | <0.01 |
| N+ | 0 | 8 |  |
| GRADE III |  |  |  |
| N− | 6 | 3 | =0.1 |
| N+ | 2 | 6 |  | pLIV1 expression also identified lymph node involvement in moderately differentiated cancers, with well differentiated tumours being predominantly pLIV1 negative (p=0.01). In addition, the relationship between pLIV1 and nodal involvement was similar in the presence or absence of vascular invasion. Similarly stratification of the pLIV1 data by pS2, showed that the association of pLIV1 and lymph node status was independent of pS2 expression in ER+ tumours (data not shown).

Thus, we have shown a highly significant association between the presence of pLIV1 gene product in primary breast cancers and lymph node involvement. Since nodal involvement still remains in the single best predictor of recurrence, we anticipate that pLIV1 expression may be extremely useful in identifying those tumours with apparent similar phenotypes (i.e. ER positivity) that display differing metastatic potential.

Sequence analysis of the pLIV1 clone (which encodes approximately 50% of the full length sequence) has as yet failed to reveal any significant homologies, but the predicted amino acid sequence has exposed an imperfect zinc finger motif.

---

What is claimed is:

1. A method of determining the risk of metastasis of a female breast tumour, which comprises determining whether a tissue sample from said tumour expresses a polypeptide comprising SEQ ID NO:2 or at least 14 continuous amino acids thereof.

2. A method according to claim 1, wherein said determining step includes contacting said sample with a labelled antibody which specifically binds to said polypeptide.

3. A method according to claim 2, wherein said antibody specifically binds to at least one of the following peptides:
   i) a peptide comprising amino acids 125–138 of SEQ ID NO: 2,
   ii) a peptide comprising amino acids 252–265 of SEQ ID NO: 2, or
   iii) a peptide comprising amino acids 418–431 of SEQ ID NO: 2.

4. A method according to claim 1, wherein said determining step includes detecting the presence of mRNA coding for said polypeptide.

5. A method according to claim 4, wherein said sample is subjected to a nucleic acid amplification process for amplifying a fragment of RNA corresponding to said mRNA coding for said polypeptide.

6. A method according to claim 4, wherein said sample is contacted with a hybridisation probe capable of specifically hybridising to said mRNA.

7. A method according to claim 1, wherein said tissue sample comprises epithelial cells.

8. A method according to claim 1, wherein the expression of estrogen receptors (ER) on cells of the tissue is additionally determined.

9. A method of predicting responsiveness to endocrine treatment of a female breast tumour, which comprises determining whether a tissue sample from said tumour expresses a polypeptide comprising SEQ ID NO:2 or at least 14 continuous amino acids thereof.

10. A method according to claim 9, wherein said determining step includes contacting said sample with a labelled antibody which specifically binds to said polypeptide.

11. A method according to claim 10, wherein said antibody specifically binds to at least one of the following peptides:

i) a peptide comprising amino acids 125–138 of SEQ ID NO: 2, ii) a peptide comprising amino acids 252–265 of SEQ ID NO: 2, or iii) a peptide comprising amino acids 418–431 of SEQ ID NO: 2.

12. A method according to claim 9, wherein said determining step includes detecting the presence of mRNA coding for said polypeptide.

13. A method according to claim 12, wherein said sample is subjected to a nucleic acid amplification process for amplifying a fragment of RNA corresponding to said mRNA coding for said polypeptides.

14. A method according to claim 9, wherein said sample is contacted with a hybridisation probe capable of specifically hybridising to said mRNA.

15. A method according to claim 9, wherein said tissue sample comprises epithelial cells.

16. A kit for use in a method of determining the responsiveness to anti-hormonal treatment of a female subject, which includes at least one antibody which specifically binds to the polypeptide of SEQ ID NO:2.

17. A kit for use in a method of determining the risk of metastasis of a breast tumour in a female subject, which includes at least one antibody which specifically binds to the polypeptide of SEQ ID NO:2.

18. A reagent comprising an antibody which specifically binds to the polypeptide of SEQ ID NO:2.

19. An isolated polypeptide consisting of SEQ ID NO:2 or at least 14 continuous amino acids thereof.

20. An isolated nucleic acid consisting of SEQ ID NO:1 or at least 42 contiguous nucleic acids thereof.

* * * * *

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 1310 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..1293

( x i ) SEQUENCE DESCRIPTION: SEQ ID NO: 1:

```
GGT TTT ATA GCC ATT TCC ATC ATC AGT TTC CTG TCT CTG CTG GGG GTT      48
Gly Phe Ile Ala Ile Ser Ile Ile Ser Phe Leu Ser Leu Leu Gly Val
 1               5                  10                  15
```

-continued

| | | | | | | | | | | | | | | | | |
|---|---|---|---|---|---|---|---|---|---|---|---|---|---|---|---|---|
| ATC | TTA | GTG | CCT | CTC | ATG | AAT | CGG | GTG | TTT | TTC | AAA | TTT | CTC | CTG | AGT | 96 |
| Ile | Leu | Val | Pro | Leu | Met | Asn | Arg | Val | Phe | Phe | Lys | Phe | Leu | Leu | Ser | |
| | | | 20 | | | | | 25 | | | | | 30 | | | |
| TTC | CTT | GTG | GCA | CTG | GCC | GTT | GGG | ACT | TTG | AGT | GGT | GAT | GCT | TTT | TTA | 144 |
| Phe | Leu | Val | Ala | Leu | Ala | Val | Gly | Thr | Leu | Ser | Gly | Asp | Ala | Phe | Leu | |
| | | 35 | | | | | 40 | | | | | 45 | | | | |
| CAC | CTT | CTT | CCA | CAT | TCT | CAT | GCA | AGT | CAC | CAC | CAT | AGT | CAT | AGC | CAT | 192 |
| His | Leu | Leu | Pro | His | Ser | His | Ala | Ser | His | His | His | Ser | His | Ser | His | |
| | | 50 | | | | 55 | | | | | 60 | | | | | |
| GAA | GAA | CCA | GCA | ATG | GAA | ATG | AAA | AGA | GGA | CCA | CTT | TTC | AGT | CAT | CTG | 240 |
| Glu | Glu | Pro | Ala | Met | Glu | Met | Lys | Arg | Gly | Pro | Leu | Phe | Ser | His | Leu | |
| 65 | | | | | 70 | | | | | 75 | | | | | 80 | |
| TCT | TCT | CAA | AAC | ATA | GAA | GAA | AGT | GCC | TAT | TTT | GAT | TCC | ACG | TGG | AAG | 288 |
| Ser | Ser | Gln | Asn | Ile | Glu | Glu | Ser | Ala | Tyr | Phe | Asp | Ser | Thr | Trp | Lys | |
| | | | | 85 | | | | | 90 | | | | | 95 | | |
| GGT | CTA | ACA | GCT | CTA | GGA | GGC | CTG | TAT | TTC | ATG | TTT | CTT | GTT | GAA | CAT | 336 |
| Gly | Leu | Thr | Ala | Leu | Gly | Gly | Leu | Tyr | Phe | Met | Phe | Leu | Val | Glu | His | |
| | | | 100 | | | | | 105 | | | | | 110 | | | |
| GTC | CTC | ACA | TTG | ATC | AAA | CAA | TTT | AAA | GAT | AAG | AAG | AAA | AAG | AAT | CAG | 384 |
| Val | Leu | Thr | Leu | Ile | Lys | Gln | Phe | Lys | Asp | Lys | Lys | Lys | Lys | Asn | Gln | |
| | | 115 | | | | | 120 | | | | | 125 | | | | |
| AAG | AAA | CCT | GAA | AAT | GAT | GAT | GAT | GTG | GAG | ATT | AAG | AAG | CAG | TTG | TCC | 432 |
| Lys | Lys | Pro | Glu | Asn | Asp | Asp | Asp | Val | Glu | Ile | Lys | Lys | Gln | Leu | Ser | |
| | 130 | | | | | 135 | | | | | 140 | | | | | |
| AAG | TAT | GAA | TCT | CAA | CTT | TCA | ACA | AAT | GAG | GAG | AAA | GTA | GAT | ACA | GAT | 480 |
| Lys | Tyr | Glu | Ser | Gln | Leu | Ser | Thr | Asn | Glu | Glu | Lys | Val | Asp | Thr | Asp | |
| 145 | | | | | 150 | | | | | 155 | | | | | 160 | |
| GAT | CGA | ACT | GAA | GGC | TAT | TTA | CGA | GCA | GAC | TCA | CAA | GAG | CCC | TCC | CAC | 528 |
| Asp | Arg | Thr | Glu | Gly | Tyr | Leu | Arg | Ala | Asp | Ser | Gln | Glu | Pro | Ser | His | |
| | | | | 165 | | | | | 170 | | | | | 175 | | |
| TTT | GAT | TCT | CAG | CAG | CCT | GCA | GTC | TTG | GAA | GAA | GAA | GAG | GTC | ATG | ATA | 576 |
| Phe | Asp | Ser | Gln | Gln | Pro | Ala | Val | Leu | Glu | Glu | Glu | Glu | Val | Met | Ile | |
| | | | 180 | | | | | 185 | | | | | 190 | | | |
| GCT | CAT | GCT | CAT | CCA | CAG | GAA | GTC | TAC | AAT | GAA | TAT | GTA | CCC | AGA | GGG | 624 |
| Ala | His | Ala | His | Pro | Gln | Glu | Val | Tyr | Asn | Glu | Tyr | Val | Pro | Arg | Gly | |
| | | 195 | | | | | 200 | | | | | 205 | | | | |
| TGC | AAG | AAT | AAA | TGC | CAT | TCA | CAT | TTC | CAC | GAT | ACA | CTC | GGC | CAG | TCA | 672 |
| Cys | Lys | Asn | Lys | Cys | His | Ser | His | Phe | His | Asp | Thr | Leu | Gly | Gln | Ser | |
| | 210 | | | | | 215 | | | | | 220 | | | | | |
| GAC | GAT | CTC | ATT | CAC | CAC | CAT | CAT | GAC | TAC | CAT | CAT | ATT | CTC | CAT | CAT | 720 |
| Asp | Asp | Leu | Ile | His | His | His | His | Asp | Tyr | His | His | Ile | Leu | His | His | |
| 225 | | | | | 230 | | | | | 235 | | | | | 240 | |
| CAC | CAC | CAC | CAA | AAC | CAC | CAT | CCT | CAC | AGT | CAC | AGC | CAG | CGC | TAC | TCT | 768 |
| His | His | His | Gln | Asn | His | His | Pro | His | Ser | His | Ser | Gln | Arg | Tyr | Ser | |
| | | | | 245 | | | | | 250 | | | | | 255 | | |
| CGG | GAG | GAG | CTG | AAA | GAT | GCC | GGC | GTC | GCC | ACT | TTG | GCC | TGG | ATG | GTG | 816 |
| Arg | Glu | Glu | Leu | Lys | Asp | Ala | Gly | Val | Ala | Thr | Leu | Ala | Trp | Met | Val | |
| | | | | 260 | | | | | 265 | | | | | 270 | | |
| ATA | ATG | GGT | GAT | GGC | CTG | CAC | AAT | TTC | AGC | GAT | GGC | CTA | GCA | ATT | GGT | 864 |
| Ile | Met | Gly | Asp | Gly | Leu | His | Asn | Phe | Ser | Asp | Gly | Leu | Ala | Ile | Gly | |
| | | | 275 | | | | | 280 | | | | | 285 | | | |
| GCT | GCT | TTT | ACT | GAA | GGC | TTA | TCA | AGT | GGT | TTA | AGT | ACT | TCT | GTT | GCT | 912 |
| Ala | Ala | Phe | Thr | Glu | Gly | Leu | Ser | Ser | Gly | Leu | Ser | Thr | Ser | Val | Ala | |
| | | 290 | | | | | 295 | | | | | 300 | | | | |
| GTG | TTC | TGT | CAT | GAG | TTG | CCT | CAT | GAA | TTA | GGT | GAC | TTT | GCT | GTT | CTA | 960 |
| Val | Phe | Cys | His | Glu | Leu | Pro | His | Glu | Leu | Gly | Asp | Phe | Ala | Val | Leu | |
| 305 | | | | | 310 | | | | | 315 | | | | | 320 | |
| CTA | AAG | GCT | GGC | ATG | ACC | GTT | AAG | CAG | GCT | GTC | CTT | TAT | AAT | GCA | TTG | 1008 |
| Leu | Lys | Ala | Gly | Met | Thr | Val | Lys | Gln | Ala | Val | Leu | Tyr | Asn | Ala | Leu | |
| | | | 325 | | | | | 330 | | | | | 335 | | | |

| | | | | | | | | | | | | | | | | |
|---|---|---|---|---|---|---|---|---|---|---|---|---|---|---|---|---|
| TCA | GCC | ATG | CTG | GCG | TAT | CTT | GGA | ATG | GCA | ACA | GGA | ATT | TTC | ATT | GGT | 1056 |
| Ser | Ala | Met | Leu | Ala | Tyr | Leu | Gly | Met | Ala | Thr | Gly | Ile | Phe | Ile | Gly | |
| | | 340 | | | | | | 345 | | | | | | 350 | | |
| CAT | TAT | GCT | GAA | AAT | GTT | TCT | ATG | TGG | ATA | TTT | GCA | CTT | ACT | GCT | GGC | 1104 |
| His | Tyr | Ala | Glu | Asn | Val | Ser | Met | Trp | Ile | Phe | Ala | Leu | Thr | Ala | Gly | |
| | | 355 | | | | | 360 | | | | | | 365 | | | |
| TTA | TTC | ATG | TAT | GTT | GCT | CTG | GTT | GAT | ATG | GTA | CCT | GAA | ATG | CTG | CAC | 1152 |
| Leu | Phe | Met | Tyr | Val | Ala | Leu | Val | Asp | Met | Val | Pro | Glu | Met | Leu | His | |
| | 370 | | | | | 375 | | | | | 380 | | | | | |
| AAT | GAT | GCT | AGT | GAC | CAT | GGA | TGT | AGC | CGC | TGG | GGG | TAT | TTC | TTT | TTA | 1200 |
| Asn | Asp | Ala | Ser | Asp | His | Gly | Cys | Ser | Arg | Trp | Gly | Tyr | Phe | Phe | Leu | |
| 385 | | | | | 390 | | | | | 395 | | | | | 400 | |
| CAG | AAT | GCT | GGG | ATG | CTT | TTG | GGT | TTT | GGA | ATT | ATG | TTA | CTT | ATT | CCA | 1248 |
| Gln | Asn | Ala | Gly | Met | Leu | Leu | Gly | Phe | Gly | Ile | Met | Leu | Leu | Ile | Pro | |
| | | | | 405 | | | | | 410 | | | | | 415 | | |
| TAT | TTG | AAC | ATA | AAA | TCG | TGT | TCG | TAT | AAA | TTT | CTA | GTT | AAG | GTT | | 1293 |
| Tyr | Leu | Asn | Ile | Lys | Ser | Cys | Ser | Tyr | Lys | Phe | Leu | Val | Lys | Val | | |
| | | | 420 | | | | | 425 | | | | | 430 | | | |

TAAATGCTAG AGTAGCT      1310

( 2 ) INFORMATION FOR SEQ ID NO: 2:

( i ) SEQUENCE CHARACTERISTICS:
        ( A ) LENGTH: 431 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

| | | | | | | | | | | | | | | |
|---|---|---|---|---|---|---|---|---|---|---|---|---|---|---|
| Gly | Phe | Ile | Ala | Ile | Ser | Ile | Ile | Ser | Phe | Leu | Ser | Leu | Leu | Gly | Val |
| 1 | | | | 5 | | | | | 10 | | | | | 15 | |
| Ile | Leu | Val | Pro | Leu | Met | Asn | Arg | Val | Phe | Phe | Lys | Phe | Leu | Leu | Ser |
| | | | 20 | | | | | 25 | | | | | 30 | | |
| Phe | Leu | Val | Ala | Leu | Ala | Val | Gly | Thr | Leu | Ser | Gly | Asp | Ala | Phe | Leu |
| | | 35 | | | | | 40 | | | | | 45 | | | |
| His | Leu | Leu | Pro | His | Ser | His | Ala | Ser | His | His | His | Ser | His | Ser | His |
| | 50 | | | | | 55 | | | | | 60 | | | | |
| Glu | Glu | Pro | Ala | Met | Glu | Met | Lys | Arg | Gly | Pro | Leu | Phe | Ser | His | Leu |
| 65 | | | | | 70 | | | | | 75 | | | | | 80 |
| Ser | Ser | Gln | Asn | Ile | Glu | Glu | Ser | Ala | Tyr | Phe | Asp | Ser | Thr | Trp | Lys |
| | | | | 85 | | | | | 90 | | | | | 95 | |
| Gly | Leu | Thr | Ala | Leu | Gly | Gly | Leu | Tyr | Phe | Met | Phe | Leu | Val | Glu | His |
| | | | 100 | | | | | 105 | | | | | 110 | | |
| Val | Leu | Thr | Leu | Ile | Lys | Gln | Phe | Lys | Asp | Lys | Lys | Lys | Lys | Asn | Gln |
| | | | 115 | | | | 120 | | | | | 125 | | | |
| Lys | Lys | Pro | Glu | Asn | Asp | Asp | Asp | Val | Glu | Ile | Lys | Lys | Gln | Leu | Ser |
| | 130 | | | | | 135 | | | | | 140 | | | | |
| Lys | Tyr | Glu | Ser | Gln | Leu | Ser | Thr | Asn | Glu | Glu | Lys | Val | Asp | Thr | Asp |
| 145 | | | | | 150 | | | | | 155 | | | | | 160 |
| Asp | Arg | Thr | Glu | Gly | Tyr | Leu | Arg | Ala | Asp | Ser | Gln | Glu | Pro | Ser | His |
| | | | | 165 | | | | | 170 | | | | | 175 | |
| Phe | Asp | Ser | Gln | Gln | Pro | Ala | Val | Leu | Glu | Glu | Glu | Glu | Val | Met | Ile |
| | | | 180 | | | | | 185 | | | | | 190 | | |
| Ala | His | Ala | His | Pro | Gln | Glu | Val | Tyr | Asn | Glu | Tyr | Val | Pro | Arg | Gly |
| | | | 195 | | | | | 200 | | | | | 205 | | |
| Cys | Lys | Asn | Lys | Cys | His | Ser | His | Phe | His | Asp | Thr | Leu | Gly | Gln | Ser |
| | 210 | | | | | 215 | | | | | 220 | | | | |

| | | | | | | | | | | | | | | |
|---|---|---|---|---|---|---|---|---|---|---|---|---|---|---|
|Asp|Asp|Leu|Ile|His|His|His|Asp|Tyr|His|His|Ile|Leu|His|His|
|225| | | |230| | | |235| | | | | |240|
|His|His|His|Gln|Asn|His|His|Pro|His|Ser|His|Ser|Gln|Arg|Tyr|Ser|
| | | | |245| | | | |250| | | | |255| |
|Arg|Glu|Glu|Leu|Lys|Asp|Ala|Gly|Val|Ala|Thr|Leu|Ala|Trp|Met|Val|
| | | | |260| | | | |265| | | | |270| |
|Ile|Met|Gly|Asp|Gly|Leu|His|Asn|Phe|Ser|Asp|Gly|Leu|Ala|Ile|Gly|
| | | |275| | | | |280| | | | |285| | |
|Ala|Ala|Phe|Thr|Glu|Gly|Leu|Ser|Ser|Gly|Leu|Ser|Thr|Ser|Val|Ala|
| |290| | | | |295| | | | |300| | | | |
|Val|Phe|Cys|His|Glu|Leu|Pro|His|Glu|Leu|Gly|Asp|Phe|Ala|Val|Leu|
|305| | | | |310| | | | |315| | | | |320|
|Leu|Lys|Ala|Gly|Met|Thr|Val|Lys|Gln|Ala|Val|Leu|Tyr|Asn|Ala|Leu|
| | | | |325| | | | |330| | | | |335| |
|Ser|Ala|Met|Leu|Ala|Tyr|Leu|Gly|Met|Ala|Thr|Gly|Ile|Phe|Ile|Gly|
| | | |340| | | | |345| | | | |350| | |
|His|Tyr|Ala|Glu|Asn|Val|Ser|Met|Trp|Ile|Phe|Ala|Leu|Thr|Ala|Gly|
| | |355| | | | |360| | | | |365| | | |
|Leu|Phe|Met|Tyr|Val|Ala|Leu|Val|Asp|Met|Val|Pro|Glu|Met|Leu|His|
| |370| | | | |375| | | | |380| | | | |
|Asn|Asp|Ala|Ser|Asp|His|Gly|Cys|Ser|Arg|Trp|Gly|Tyr|Phe|Phe|Leu|
|385| | | |390| | | | |395| | | | | |400|
|Gln|Asn|Ala|Gly|Met|Leu|Leu|Gly|Phe|Gly|Ile|Met|Leu|Leu|Ile|Pro|
| | | | |405| | | | |410| | | | |415| |
|Tyr|Leu|Asn|Ile|Lys|Ser|Cys|Ser|Tyr|Lys|Phe|Leu|Val|Lys|Val| |
| | | |420| | | | |425| | | | |430| | |

( 2 ) INFORMATION FOR SEQ ID NO: 3:

( i ) SEQUENCE CHARACTERISTICS:
        ( A ) LENGTH: 2404 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO: 3:

```
GGTTTTATAG CCATTTCCAT CATCAGTTTC CTGTCTCTGC TGGGGGTTAT CTTAGTGCCT    60
CTCATGAATC GGGTGTTTTT CAAATTTCTC CTGAGTTTCC TTGTGGCACT GGCCGTTGGG   120
ACTTTGAGTG GTGATGCTTT TTACACCTT CTTCCACATT CTCATGCAAG TCACCACCAT   180
AGTCATAGCC ATGAAGAACC AGCAATGGAA ATGAAAAGAG GACCACTTTT CAGTCATCTG   240
TCTTCTCAAA ACATAGAAGA AAGTGCCTAT TTTGATTCCA CGTGGAAGGG TCTAACAGCT   300
CTAGGAGGCC TGTATTTCAT GTTTCTTGTT GAACATGTCC TCACATTGAT CAAACAATTT   360
AAAGATAAGA AGAAAAAGAA TCAGAAGAAA CCTGAAAATG ATGATGATGT GGAGATTAAG   420
AAGCAGTTGT CCAAGTATGA ATCTCAACTT TCAACAAATG AGGAGAAAGT AGATACAGAT   480
GATCGAACTG AAGGCTATTT ACGAGCAGAC TCACAAGAGC CCTCCCACTT TGATTCTCAG   540
CAGCCTGCAG TCTTGGAAGA AGAAGAGGTC ATGATAGCTC ATGCTCATCC ACAGGAAGTC   600
TACAATGAAT ATGTACCCAG AGGGTGCAAG AATAAATGCC ATTCACATTT CCACGATACA   660
CTCGGCCAGT CAGACGATCT CATTCACCAC CATCATGACT ACCATCATAT TCTCCATCAT   720
CACCACCACC AAAACCACCA TCCTCACAGT CACAGCCAGC GCTACTCTCG GGAGGAGCTG   780
AAAGATGCCG GCGTCGCCAC TTTGGCCTGG ATGGTGATAA TGGGTGATGG CCTGCACAAT   840
```

-continued

```
TTCAGCGATG GCCTAGCAAT TGGTGCTGCT TTTACTGAAG GCTTATCAAG TGGTTTAAGT      900
ACTTCTGTTG CTGTGTTCTG TCATGAGTTG CCTCATGAAT TAGGTGACTT TGCTGTTCTA      960
CTAAAGGCTG GCATGACCGT TAAGCAGGCT GTCCTTTATA ATGCATTGTC AGCCATGCTG     1020
GCGTATCTTG GAATGGCAAC AGGAATTTTC ATTGGTCATT ATGCTGAAAA TGTTTCTATG     1080
TGGATATTTG CACTTACTGC TGGCTTATTC ATGTATGTTG CTCTGGTTGA TATGGTACCT     1140
GAAATGCTGC ACAATGATGC TAGTGACCAT GGATGTAGCC GCTGGGGGTA TTTCTTTTTA     1200
CAGAATGCTG GGATGCTTTT GGGTTTTGGA ATTATGTTAC TTATTCCATA TTTGAACATA     1260
AAATCGTGTT CGTATAAATT TCTAGTTAAG GTTAAATGC TAGAGTAGCT TAAAAAGTTG      1320
TCATAGTTTC AGTAGGTCAT AGGGAGATGA GTTTGTATGC TGTACTATGC AGCGTTTAAA     1380
GTTAGTGGGT TTTGTGATTT TTGTATTGAA TATTGCTGTC TGTTACAAAG TCAGTTAAAG     1440
GTACGTTTTA ATATTTAAGT TATTCTATCT TGGAGATAAA ATCTGTATGT GCAATTCACC     1500
GGTATTACCA GTTTATTATG TAAACAAGAG ATTTGGCATG ACATGTTCTG TATGTTTCAG     1560
GGAAAAATGT CTTTAATGCT TTTTCAAGAA CTAACACAGT TATTCCTATA CTGGATTTTA     1620
GGTCTCTGAA GAACTGCTGG TGTTTAGGAA TAAGAATGTG CATGAAGCCT AAAATACCAA     1680
GAAAGCTTAT ACTGAATTTA AGCAAAGAAA TAAAGGAGAA AAGAGAAGAA TCTGAGAATT     1740
GGGGAGGCAT AGATTCTTAT AAAAATCACA AAATTTGTTG TAAATTAGAG GGGAGAAATT     1800
TAGAATTAAG TATAAAAAGG CAGAATTAGT ATAGAGTACA TTCATTAAAC ATTTTTGTCA     1860
GGATTATTTC CCGTAAAAAC GTAGTGAGCA CTCTCATATA CTAATTAGTG TACATTTAAC     1920
TTTGTATAAT ACAGAAATCT AAATATATTT AATGAATTCA AGCAATATAC ACTTGACCAA     1980
GAAATTGGAA TTTCAAAATG TTCGTGCGGG TTATATACCA GATGAGTACA GTGAGTAGTT     2040
TATGTATCAC CAGACTGGGT TATTGCCAAG TTATATATCA CCAAAAGCTG TATGACTGGA     2100
TGTTCTGGTT ACCTGGTTTA CAAAATTATC AGAGTAGTAA AACTTTGATA TATATGAGGA     2160
TATTAAAACT ACACTAAGTA TCATTTGATT CGATTCAGAA AACTTTGATA TATATGAGGA     2220
TATTAAAACT ACACTAAGTA TCATTTGATT CGATTCAGAA AGTACTTTGA TATCTCTCAG     2280
TGCTTCAGTG CTATCATTGT GAGCAATTGT CTTTATATAC GGTACTGTAG CCATACTAGG     2340
CCTGTCTGTG GCATTCTCTA GATGTTTCTT TTTACACAA TAAATTCCTT ATATCAGCTT      2400
GAAA                                                                  2404
```